United States Patent [19]

Holmblad et al.

[11] Patent Number: 5,173,302

[45] Date of Patent: Dec. 22, 1992

[54] HYDROPHILIC PRESSURE SENSITIVE ADHESIVE FOR TOPICAL ADMINISTRATION OF HYDROPHOBIC DRUGS

[75] Inventors: Carolann M. Holmblad, Cambridge; Joan M. Bergstrom, Minneapolis; Terese A. Bartlett, Circle Pines, all of Minn.

[73] Assignee: Medtronic, Inc., Minneapolis, Minn.

[21] Appl. No.: 590,648

[22] Filed: Sep. 28, 1990

[51] Int. Cl.$^5$ ........................ A61F 13/00; A61K 47/32
[52] U.S. Cl. .................................. 424/448; 424/449; 514/772.5; 514/772.6
[58] Field of Search ................ 424/448, 486, 487, 449

[56] References Cited

U.S. PATENT DOCUMENTS

| | | | |
|---|---|---|---|
| 2,973,300 | 2/1961 | Farrar et al. | 424/94.2 |
| 3,214,338 | 10/1965 | Ehrlich | 514/772.4 |
| 3,536,809 | 10/1970 | Applezweig | 424/435 |
| 3,592,930 | 7/1971 | Katz et al. | 424/243 |
| 3,598,122 | 8/1971 | Zaffaroni et al. | 128/268 |
| 3,598,123 | 8/1971 | Zaffaroni et al. | 128/268 |
| 3,632,740 | 1/1972 | Robinson et al. | 424/28 |
| 3,731,683 | 5/1973 | Zaffaroni et al. | 128/268 |
| 3,734,097 | 5/1973 | Zaffaroni | 128/268 |
| 3,742,951 | 7/1973 | Zaffaroni | 128/268 |
| 3,888,995 | 6/1975 | Katz et al. | 424/358 |
| 3,929,741 | 12/1975 | Laskey | 260/79.3 |
| 3,931,087 | 1/1976 | Baatz et al. | 260/29.6 |
| 3,948,254 | 4/1976 | Zaffaroni | 128/127 |
| 4,017,615 | 4/1977 | Shastri et al. | 424/241 |
| 4,191,743 | 3/1980 | Klemm et al. | 424/28 |
| 4,210,633 | 7/1980 | Takuri et al. | 424/80 |
| 4,230,105 | 10/1980 | Harwood | 128/156 |
| 4,286,592 | 9/1981 | Chandrasekaran | 128/260 |
| 4,292,301 | 9/1981 | Keith et al. | 424/28 |
| 4,307,717 | 12/1981 | Hymes et al. | 128/156 |
| 4,391,278 | 7/1983 | Cahalan et al. | 128/640 |
| 4,409,206 | 10/1983 | Stricker | 424/81 |

(List continued on next page.)

OTHER PUBLICATIONS

Product brochure for "LIDEX® (fluocinonide) Gel 0.05%", Syntex Laboratories, Inc., Jan. 1985.

(List continued on next page.)

Primary Examiner—Thurman K. Page
Assistant Examiner—L. Horne
Attorney, Agent, or Firm—Harold R. Patton; Daniel W. Latham

[57] ABSTRACT

Novel hydrogel formulations useful as adhesive reservoirs for topical or transdermal drugs employ as the polymer base a crosslinked polymer or copolymer of 2-acrylamido-2-methylpropanesulfonic acid or a salt thereof. The gels are prepared from polymerizable compositions comprising:

20%–50% of a monofunctional monomer component, at least 75% of said component comprising 2-acrylamido-2-methylpropane sulfonic acid or a salt thereof, the balance being selected from the group consisting of acrylic acid, water soluble acrylic functional monomers and vinyl pyrrolidone;

30%–50% of a glycol component selected from the group consisting of compounds of the formula $$HO-(C_2H_4O)_n-H,$$

$$HO-(C_3H_6O)_m-H$$

and mixtures thereof, where n is in the range of about 4 to about 16 and m is 1–4;

between about 0.02% and about 0.20% of a crosslinking monomer;

an amount of a free radical polymerization initiator effective for initiating polymerization of said monofunctional monomer and crosslinking monomer components; and a therapeutically effective amount of a topically or transdermally deliverable drug, at least about 60% of said drug being dissolved in the formulation.

24 Claims, 2 Drawing Sheets

U.S. PATENT DOCUMENTS

| | | | |
|---|---|---|---|
| 4,470,962 | 9/1984 | Keith et al. | 424/28 |
| 4,477,325 | 10/1984 | Osburn | 204/159.12 |
| 4,551,490 | 11/1985 | Doyle et al. | 524/22 |
| 4,593,053 | 6/1986 | Jeyne et al. | 523/111 |
| 4,605,548 | 8/1986 | Ushiyama et al. | 424/15 |
| 4,655,768 | 4/1987 | Marecki et al. | 604/897 |
| 4,668,506 | 5/1987 | Bawa et al. | 424/429 |
| 4,675,009 | 6/1987 | Hymes et al. | 604/304 |
| 4,713,244 | 12/1987 | Bawa et al. | 424/429 |
| 4,738,257 | 4/1988 | Meyer et al. | 128/156 |
| 4,768,523 | 9/1988 | Cahalan et al. | 128/785 |
| 4,931,279 | 6/1990 | Bawa et al. | 424/429 |

OTHER PUBLICATIONS

Product brochure for "ACTIDERM ® Dermatological Patch" Convatec, A Squibb Company, Sep. 1987.

Ad for "ACTIDERM ® Dermatological Patch, The multi-action vehicle", E.R. Squibb & Sons, Inc. Jan. 1989.

Instructions for Use "RESTORE ®Dressing for Psoriasis", Hollister Incorporated, 1988.

Ad/Directions for RESTORE ® Dressing for Psoriasis, "A Sterile, Occlusive Dressing for the Management of Psoriasis" Hollister Inc.

Product brochure for "CORTRIL ® Hydrocartisone Topical Ointment 1.0%", Pfizer Laboratories Div., Aug. 1987.

Product brochure for "FOUGERA Hydrocortisone Cream U.S.P." E. Fougera & Co., Oct. 1984.

Product brochure for "FOUGERA Hydrocortisone Ointment U.S.P.", E. Fougera & Co., May 1985.

Product brochure for "HYTONE ® (hydrocortisone) Cream, Lotion, Ointment", Dermik Laboratories, Inc., Jun. 1988.

Product brochure for "LIDEX ® (fluocinonide) Topical Solution 0.05%" Syntex Laboratories, Inc., Nov. 1985.

Product brochure for "LIDEX ® (flucinoide) Cream 0.05%", Syntex Laboratories, Inc.

HYDROPHILIC PRESSURE SENSITIVE ADHESIVE FOR TOPICAL ADMINISTRATION OF HYDROPHOBIC DRUGS

FIELD OF THE INVENTION

This invention pertains to adhesive matrix materials for transdermal or topical administration of medicines.

BACKGROUND OF THE INVENTION

U.S. Pat. Nos. 4,017,615, 3,888,995 and 3,592,930 pertain to ointment-like vehicle for corticosteroid drugs and the like.

References which disclose film formers as ingredients for topically administered dry formulations include U.S. Pat. Nos. 2,973,300, 3,214,338 and 4,210,633.

Bandage-like devices for delivering drugs topically or transdermally are described in U.S. Pat. Nos. 3,598,123, 4,191,743, 4,605,548, 4,655,768, 4,409,206, 4,286,592, 4,230,105, 3,948,254, 3,742,951, 3,734,097 and 3,731,683. Such devices may include separate adhesion and drug reservoir layers.

U.S. Pat. No. 3,536,809 discloses a mixture of a drug such as progesterone dispersed in a polyalkyleneglycol impregnated into a fabric strip which may be retained in the mouth to administer the drug through the buccal mucosa.

Considered more pertinent to the invention hereof are polymeric dispersion matrix materials which have skin adhesive properties and have a drug dispersed directed into the matrix.

In U.S. Pat. No. 3,632,740 it is suggested to incorporate a drug such as a corticosteroid into a pressure sensitive rubbery adhesive layer on a flexible backing.

In U.S. Pat. No. 4,292,301 there is disclosed a polymeric diffusion matrix said to permit sustained release of ephedrine, the matrix comprising a polar plasticizer such as glycerol or polyethylene glycol (MW 1000), polyvinyl alcohol, polyvinyl pyrrolidone and ephedrine.

U.S. Pat. No. 4,470,962 discloses a polymeric diffusion matrix said to be capable of sustained release of a drug comprising glycerol, polyvinylalcohol, a water soluble polymer with hydration sites, a drug dispersed therein and water.

U.S. Pat. Nos. 4,307,717 and 4,675,009 describe bandage materials which include a backing element and a substrate comprising a matrix material comprising a solid phase formed of a polysaccharide or certain synthetic polymers and a liquid phase consisting of a hydric alcohol, carbohydrates and/or proteins in an aqueous solution. The matrix material also contains a medicament suspended or dissolved therein.

U.S. Pat. No. 4,593,053 discloses polyvinylalcohol/polyvinyl pyrrolidone based gels with non-syneresing adhesive characteristics. In one embodiment the gels contain an ionic drug which can be iontophoretically delivered. Tacifiers such as poly-2-acrylamido-2-methylpropane sulfonic acid may be added to the formulation at levels of 2%-20%.

Hydrogel materials based on polymerized 2-acrylamido-2-methylpropane sulfonate salts are known as electrode materials from U.S. Pat. Nos. 4,391,278 and 4,768,523. In U.S. Pat. No. 4,391,278 a tape electrode is disclosed which includes a gel comprising polymerized 2-acrylamido-2-methane sulfonic acid or a salt thereof, water and/or an alcohol to give electrically conductive, flexible skin adhering properties. All of the example formulations employing an alcohol utilize glycerol although propylene glycol and sorbitol are also mentioned as useful.

SUMMARY OF THE INVENTION

The present invention pertains to novel hydrogel formulations useful as adhesive reservoirs for topical or transdermally administered drugs. The formulations employ as the polymer base a crosslinked polymer or copolymer of 2-acrylamido-2-methylpropanesulfonic acid or a salt thereof, preferably the sodium salt.

The invention also pertains to polymerizable formulations, curable to produce such adhesives on a backing, in particular such formulations comprise a formulation comprising:

20%-50% of a monofunctional monomer component, at least 75% of said component comprising 2-acrylamido-2-methylpropane sulfonic acid or a salt thereof, the balance being selected from the group consisting of acrylic acid, water soluble acrylic functional monomers and vinyl pyrrolidone;

30%-50% of a glycol component selected from the group consisting of compounds of the formula

and mixtures thereof, where n is in the range of about 4 to about 16 and m is 1-4;

between about 0.02% and about 0.20% of a crosslinking monomer;

an amount of a free radical polymerization initiator effective for initiating polymerization of said monofunctional monomer and crosslinking monomer components; and a therapeutically effective amount of a topically or transdermally deliverable drug, at least about 60% of said drug being dissolved in the formulation.

In the preferred embodiment the drug is a hydrophobic drug. Most preferably the compositions are curable by UV irradiation.

The invention also comprises cured gels produced from formulations as described above, particularly of a laminate on a suitable backing material to form an adhesive bandage or patch.

DETAILED DESCRIPTION OF THE INVENTION

The polymerized matrix gel material of the invention is tacky, light to moderately adhesive and leaves little or no residue on the skin when removed. That is, its cohesive strength is sufficient to overcome its adhesive properties.

Figure 2:
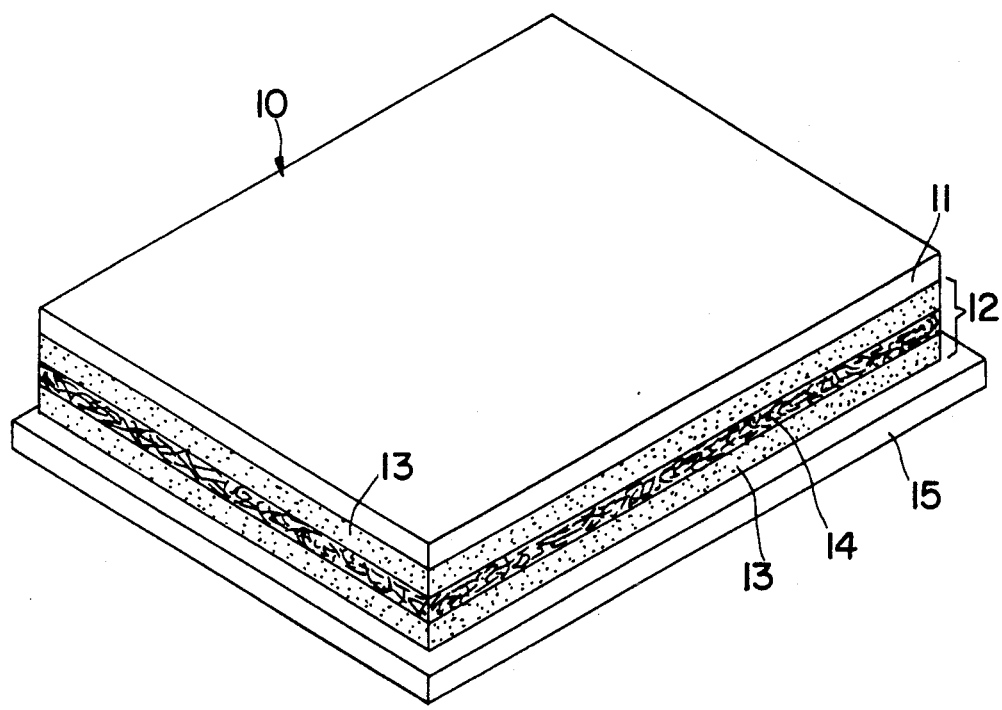
FIG. 2 is a perspective view of a bandage employing a drug containing gel adhesive of the invention.

Suitably the polymerized matrix gel material is used as a thin layer on a flexible backing material to produce an adhesive bandage-like structure. The preferred bandage, shown in FIG. 2, is a laminate structure 10 having a flexible backing material as the top layer 11; a supported gel matrix layer 12 which comprises the cured drug containing adhesive gel 13 and includes in the central portion thereof a reinforcing fabric 14; and a bottom peelable protective layer 15 which is removed when used. A backing material which is preferred for its moisture transmission properties is a 2.5 mil flexible ether type polyurethane. However, an elastomeric polyester such as Hytrel ™ or a polyethylene film material may also be used. Useful reinforcing fabrics are spun bonded polyester or polyamide fabrics about 5 mils thick having a weight of about 0.4–1 ounce per square yard. The central gel and reinforcing fabric layer is suitably about 0.05"–0.25" thick, preferably 0.15" thick. The bottom peelable release layer, which is suitably about 5 mil thick, may be a polyester such as Mylar ™ polyester, various copolyesters, optically clear styrene or other suitable release sheet material.

The polymerized gels of the invention are based on a monofunctional monomer component which is predominantly (i.e., at least about 80% by weight) 2-acrylamido-2-methylpropanesulfonic acid or a soluble salt thereof. The acid monomer is sold by Lubrizol Corp. under the trademark AMPS ®. Most preferably the base monomer is the sodium salt ("Na AMPS"). This monomer will polymerize free radically with common initiators, including peroxy compounds and UV photoinitiators. The monomer is capable of polymerizing with crosslinking monomers in the presence of water and/or alcohols to produce shape retaining gels which are flexible and adhesive. Suitabley the NaAMPS monomer is employed as a 40-60% solution in water.

The 2-acrylamido-2-methylpropanesulfonic acid monomer is suitably copolymerized with minor amounts of additional water soluble monofunctional monomers such as acrylic acid, vinyl pyrrolidone or water compatible acrylic functional monomers, particularly water miscible acrylamide functional monomers. Most preferably it is copolymerized with acrylic acid, which suitably comprises up to 25% of the total monofunctional monomer, preferably about 6%-18%.

A small amount of crosslinking monomer is also incorporated into the inventive formulations. Crosslinking monomers have 2 or more copolymerizable groups and may include prepolymer compounds with the requisite functionality. Such monomers include di and poly acrylate or acrylamide functional compounds. Particularly preferred is methylene-bis-acrylamide ("MBA") which is employed in the examples herein as a 1% solution in water.

A particular aspect of the invention is the criticality of the humectant component when hydrophobic drugs are employed. Polyols such as glycerol (which has been the preferred humectant in the prior art polymeric drug dispersion matrix formulations) produce unacceptable cured products in which the drug has little or no solubility in the cured matrix. In the products of the invention the drug does not separate out into noticeably discrete particles although some opacity may be encountered. In the preferred embodiments the gels are clear or only slightly cloudy.

The drugs used in the inventive formulations must have substantial solubility, i.e. at least about 60% dissolved, in the humectant in both the monomer formulations and the polymer matrix. This property is important to maintaining consistent polymer properties and in assuming that the drug can be reliably delivered to the patient's skin. Preferably the drug is at least about 80% dissolved in the humectant.

At least one drug is substantially dissolved in the polymeric gels of the invention. The type of drug which may be employed may be any drug which is capable of being transdermally or topically administered to a patent and which can be substantially dissolved in the polymerizable and polymerized formulations at effective dosage levels. A particular benefit of the invention is the ability to dissolve and deliver hydrophobic drugs in a hydrophilic adhesive hydrogel. The most preferred class of drugs useful in the invention are adrenocorticosteroids, such as hydrocortisone and its pharmaceutically acceptable esters, e.g. acetate, butyrate, valerate, and hemisuccinate esters; betamethasone and its pharmaceutically acceptable esters, e.g. adamantoate, benzoate, diproprionate, valerate and divalerate esters; fluocinoide; and triamicinolone acetonide. Other drugs including antinfectives such as tolnaflate, analgesics such as salicylic acid and anesthetics such as lidocaine may be used. Depending on solubility and desired dosage factors, the drug may suitably be at levels of a few ppm to 20% or more based on the total weight of the polymerizable composition. Typical levels will range from 0.05%-15%. Suitable levels for hydrocortisone range up to about 1%, whereas the hemisuccinate may be employed at levels of 2.5% or more by weight.

While the invention provides unique compatibility advantages when the drug is a hydrophobic drug, it is not necessary that the drug be a hydrophobic drug to practice the invention. For instance, water soluble antibiotics and other antiinfective agents are also suitably used in the drug delivery gels of the invention. Examples of such antiinfective agents include erythromycin, neomycin sulfate, gentamicin or its sulfate, sodium cephalothin, polyvinylpyrrolidone-iodine complex and the like.

The compositions of the invention may also employ other ingredients such as thickeners colorants, reinforcing agents, etc., which do not materially detract from the performance of the cured polymeric gels for their intended purposes.

As previously mentioned, curing of the composition may be accomplished by conventional techniques. For instance, the polymerization procedures of Examples 1–9 of U.S. Pat. No. 4,391,278 may be readily adapted by those skilled in the art for use with formulations as claimed herein to produce acceptable polymer gel products. However, it is most preferred that the compositions be photocured. For photocuring an effective amount of a conventional photoinitiator is employed. Suitably the photoinitiator is added at a level of between about 75 ppm and 1500 ppm. Conveniently the photoinitiator may be added as a solution in a compatible solvent such as isopropanol.

Suitable photoinitiator compounds include benzoin, benzophenone, and acetophenone derivatives such as dimethoxyacetophenone or diethoxyacetophenone, and (1-hydroxy)cyclohexyl phenyl ketone sold under the tradename Irgacure ™ 184.

The invention is illustrated by the following non-limiting examples.

EXAMPLE 1

A gel material of the invention was prepared by combining (where parts are by weight) 45.25 parts of a 58% solution of NaAMPS in water, 8 parts of a 1% N,N-methylene-bis-acrylamide solution in deionized water and a drug/humectant premix (comprising 39.60 parts polyethylene glycol M.W.=300 (PEG 300) and 0.99 parts hydrocortisone stirred together for 30 minutes) in a mixing tank and stirring for one hr. at 100 rpm. Silica, 2.48 parts, was added and stirred for an additional 30 min. Acrylic acid, 2.77 parts, was then added and the mixture stirred an additional 20 min. A photoinitiator, Irgacure TM 184 was then added (1 part of a 3% solution in isopropanol) and the mixture stirred for 10 min. longer. The mixture was degassed under vacuum, coated through a mesh reinforcement layer of spun bonded polyester (Reemay 2055) onto a polyester sheet material (5 mil Mylar TM). The coating/reinforcing fabric layer was 0.15" thick. The composition was then cured with UV irradiation of 1.77 mW/cm$^2$ from a 365 nm Hg vapor lamp for 1.5 minutes. The cured gel was covered with a polyurethane top liner (2.5 mil Bertek TM Medifilm U426) to give a laminate which could be cut into desired shapes. The bottom polyester layer is readily peeled off to expose the gel surface which is slightly to moderately tacky and leaves no noticeable residue when placed on skin and then removed. The gel has sufficient adhesion to remain on skin for at least 8 hours.

EXAMPLE 2

A blank patch material prepared as in Example 1, except that no drug was incorporated therein, was used as a test receptor material to evaluate bioavailability of the hydrocortisone in the products of the invention and in commercial hydrocortisone ointments.

A blank gel patch was covered with a thin polycarbonate membrane through which the drug had been demonstrated to pass freely. Test patches similarly prepared except that they contained 0.5% and 1.0% hydrocortisone were applied to the top side of the polycarbonate membrane and maintained at 37° C. Contact times of 1 hr, 2 hrs, 4 hrs, 6 hrs, 8 hrs and 24 hrs were obtained after which the Blank patch was separated from the membrane, and extracted with methanol. The amount of hydrocortisone which had migrated from the test patch to the Blank patch was determined on the extract. Comparative measurements were made using commercial hydrocortisone ointments applied to the top side of the polycarbonate membrane. Results are shown in FIG. 1 where the various formulations tested are represented as follows.

TABLE I

| | Test Patch |
|---|---|
| 1 | 1% hydrocortisone |
| 2 | 0.5% hydrocortisone |
| | Comparative Ointments |
| A | Cortril TM 1% hydrocortisone |
| B | Fougera Cream 1% hydrocortisone |
| C | Fougera Ointment 1% hydrocortisone |
| D | NutraCream 1% hydrocortisone |
| E | Hytone Ointment 1% hydrocortisone |

Figure 1:
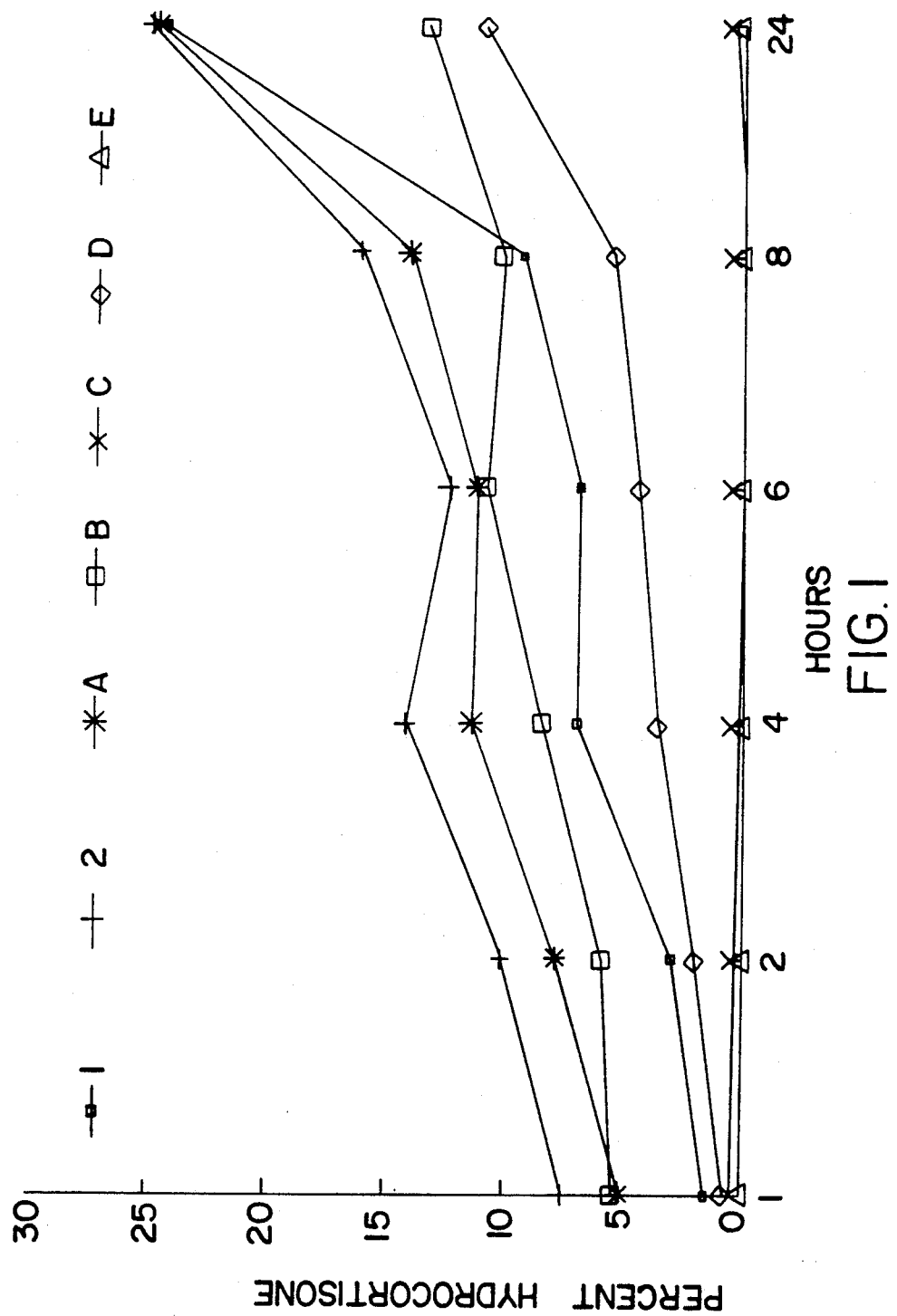
FIG. 1 is a graph comparing migration results of hydrocortisone from gel adhesive materials of the invention against several commercial hydrocortisone containing ointments and creams.

FIG. 1 demonstrates that hydrocortisone migrated as easily from both the 0.5% and 1.0% test patches of the invention as it did from the most mobile ointment formulations (1% Cortril TM).

EXAMPLE 3

Formulations were prepared having the following ingredients:

TABLE II

| Ingredient | % By Weight |
|---|---|
| 58% NaAMPS soln. | 45.7 |
| 1% MBA Solution | 8.0 |
| Acrylic Acid | 2.8 |
| Silica | 2.5 |
| Hydrocortisone | 1.0 |
| Humectant | 40.0 |

Different humectants were used as shown in Table III. The formulations were observed for suitable solubility in the monomer formulation and those showing reasonable compatibility of the drug were cured by adding 1% by weight of a 3% solution in isopropanol of (1-hydroxy)cyclohexyl phenyl ketone (Irgacure TM 184) and irradiating as in Example 1. The results shown in the Table III demonstrate the criticality of the selection of humectant.

TABLE III

| Formulations | Humectant | Observation |
|---|---|---|
| 3 | PEG 200 | Acceptable gel, slightly opaque. Hydrocortisone mostly dissolved. |
| 4 | PEG 400 | Slightly opaque. Hydrocortisone mostly dissolved. |
| 5 | PEG 600 | Good gel. Hydrocortisone nearly all dissolved |
| 6 | glycerol | Unacceptable. Dissolution of hydrocortisone particles was not apparent in uncured formulation. Curing was attempted but hydrocortisone particles were observed in the cured gel as well. |
| 7 | propylene glycol | Good product. Hydrocortisone totally dissolved in uncured formulation. Cured gel was clear and somewhat softer than PEG based gels. |
| 8 | dipropylene glycol | Good product. Hydrocortisone totally dissolved in uncured formulation. Cured gel was clear and somewhat softer than PEG based gels. |
| Comparative Formulations | | |
| F | Sorbitol | Unacceptable. No dissolution of hydrocortisone in the uncured formulation. |
| G | Polyol-P | Unacceptable. No dissolution of hydrocortisone in the uncured formulation. |
| H | 2-methyl-2,4-pentanediol | Unacceptable. Hydrocortisone totally dissolved in uncured formulation but phase separated on polymerization giving opaque non-tacky material. |
| I | PPG 425 | Unacceptable. Clear uncured solution but drug came out of solution when cured. Gel is opaque and tack free. Syneresis of the humectant occurred. |
| J | PPG 725 | Unacceptable. The uncured formulation was opaque |

TABLE III-continued

| Formulations | Humectant | Observation |
| --- | --- | --- |
| | | and too thick to work with. |
| K | Polyglycol P-2000 | Unacceptable. A very thick opaque white formulation. Abandoned without curing. |
| L | Polyglycol 15-200 | Unacceptable. Clear solution uncured but an opaque tack-free clear cured product in which the drug appeared to have come out of solution. |
| M | Pluronic L10 | Unacceptable. Opaque tack-free cured product. |
| N | Pluronic L35 | Unacceptable. Opaque tack-free cured product. |
| O | Pluronic L64 | Unacceptable. Uncured formulation was too thick to stir. Abandoned without curing. |

EXAMPLE 4

Formulations were prepared as shown in Table IV. In all cases acceptable moderately adhesive gels were obtained upon photocuring after adding 0.5%-1.0% of a 3% Irgacure ™ 184 solution.

TABLE IV

| Ingredient | 9 | 10 | 11 | 12 | 13 | 14 | 15* | 16 | 17 |
| --- | --- | --- | --- | --- | --- | --- | --- | --- | --- |
| NaAMPS | 49.7 | 50.2 | 41 | 48.6 | 47.7 | 47.7 | 46.2 | 46.65 | 46.6 |
| 1% MBA | 4.0 | 4.0 | 4 | 6.0 | 6.0 | 6.0 | 6.0 | 8.0 | 8.0 |
| Silica | 2.5 | 2.5 | — | 2.5 | 2.5 | 2.5 | 2.5 | 2.5 | 2.5 |
| PEG 300 | 40.0 | 40.0 | 35 | 40.0 | 40.0 | 30.0 | 40.0 | 40.0 | 40.0 |
| Acrylic Acid | 2.8 | 2.8 | 5 | 2.8 | 2.8 | 2.8 | 2.8 | 2.8 | 2.8 |
| Lidocaine | 1.0 | 0.5 | — | — | — | — | — | — | — |
| Salicyclic Acid | — | — | 15 | — | — | 10.0 | — | — | — |
| Hydrocortisone Hemisuccinate | — | — | — | — | — | — | 2.5 | — | — |
| Tolnaflate | — | — | — | — | 1.0 | 1.0 | — | — | — |
| Betamethazone Valerate | — | — | — | 0.10 | — | — | — | — | — |
| Fluocinonide | — | — | — | — | — | — | — | 0.05 | — |
| Triamcinolone Acetonide | — | — | — | — | — | — | — | — | 0.10 |

*Neutralized to pH 7.38 with 50% NaOH before polymerization

What is claimed is:

1. A polymerizable composition comprising:
   20%-50% of a monofunctional monomer component, at least 75% of said component comprising 2-acrylamido-2-methylpropane sulfonic acid or a salt thereof, the balance being selected from the group consisting of acrylic acid, water soluble acrylic functional monomers and vinyl pyrrolidone;
   30%-50% of a hymectant selected from the group consisting of compounds of the formula $HO-(C_2H_4O)_n-H$, $HO-(C_3H_6O)_m-H$ and mixtures thereof, where n is in the range of about 4 to about 16 and m is 1-4;
   between about 0.02% and about 0.20% of a crosslinking monomer;
   an amount of a free radical polymerization initiator effective for initiating polymerization of said monofunctional monomer and crosslinking monomer components; and
   a therapeutically effective amount of a topically or transdermally deliverable drug, at least about 60% of said drug being dissolved in the formulation.

2. A composition as in claim 1 wherein said drug is a hydrophobic drug.

3. A composition as in claim 2 wherein the hydrophobic drug is a corticosteroid.

4. A composition as in claim 3 wherein the hydrophobic drug is selected from the group consisting of hydrocortisone and its pharmaceutically acceptable esters, betamethasone and its pharmaceutically acceptable esters, fluocinoide and trimcinolone acetonide.

5. A composition as in claim 4 wherein the hydrophobic drug is hydrocortisone.

6. A composition as in claim 5 wherein the hydrocortisone is present at a level of about 0.5-1% by weight.

7. A composition as in claim 3 wherein the hydrophobic drug is hydrocortisone hemisuccinate.

8. A composition as in claim 7 wherein the hydrocortisone hemisuccinate is present at a level of about 0.5-3.0% by weight.

9. A composition as in claim 7 having a neutral pH.

10. A composition as in claim 1 wherein the drug is an analgesic, antiinfective or anesthetic.

11. A composition as in claim 1 wherein the monofunctional monomer component is present at a level of between about 25% and about 50%.

12. A composition as in claim 11 wherein the monofunctional monomer component includes acrylic acid in addition to said 2-acrylamido-2-methylpropane sulfonic acid or salt thereof.

13. A composition as in claim 12 wherein the acrylic acid comprises between about 6% and about 18% of said monofunctional monomer component.

14. A composition as in claim 1 wherein the humectant is polyethylene glycol 300.

15. A tacky, drug containing adhesive leaving substantially no residue when pulled from skin comprising a cured product of the formulation of claim 1.

16. An adhesive as in claim 15 wherein the drug is substantially dissolved in said cured formulation.

17. An adhesive as in claim 15 wherein the drug is a corticosteroid, antiinfective, analgesic or anesthetic.

18. An adhesive as in claim 17 wherein the drug is selected from hydrocortisone and its pharmaceutically acceptable esters, betamethasone and its pharmaceutically acceptable esters, fluocinoide and triaminicinolone acetonide.

19. An adhesive as in claim 18 wherein the drug is hydrocortisone or an ester thereof.

20. An adhesive as in claim 15 wherein the drug is a hydrophobic drug.

21. A therapeutic patch for topical or transdermal application of a drug having a laminate structure comprising a flexible top liner, a reinforced layer of an adhesive as in claim 15 and a peelable bottom release liner.

22. A patch as in claim 21 wherein the flexible top liner is a flexible polyether polyurethane sheet material, the adhesive is reinforced with a fabric material and the bottom release liner is a polyester sheet material.

23. A patch as in claim 22 wherein the reinforcing fabric is a spun bonded polyester fabric.

24. A patch as in claim 21 prepared by applying a polymerizable composition as in claim 1 to said bottom liner through said reinforcing fabric, photocuring the polymerizable composition and then covering the composition with the bottom liner.

* * * * *